Nov. 25, 1958 E. B. PARKER Plant Pat. 1,773
CHRYSANTHEMUM
Filed March 3, 1958
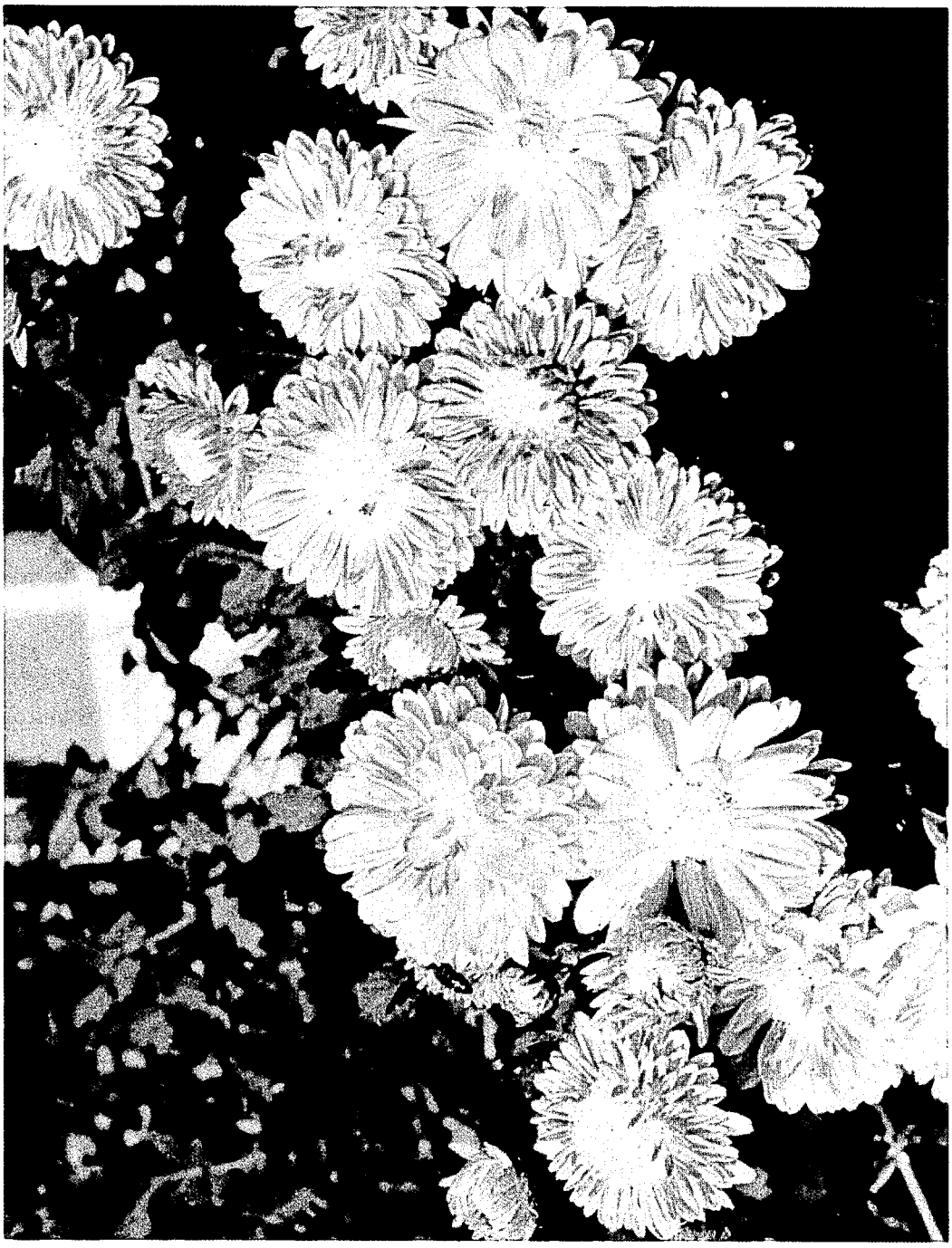
INVENTOR.
ELIZABETH B. PARKER
BY
John Joseph Hall
ATTORNEY.

United States Patent Office

Plant Pat. 1,773
Patented Nov. 25, 1958

1,773

CHRYSANTHEMUM

Elizabeth B. Parker, Los Angeles, Calif.

Application March 3, 1958, Serial No. 718,933

1 Claim. (Cl. 47—60)

The present invention relates to a new and distinct variety of chrysanthemum plant obtained by crossing the unpatented variety "Anemone" (H. J. Balough) with an unnamed and unpatented bronze daisy chrysanthemum.

This cross was made for the purpose of obtained a new chrysanthemum variety with a sweet fragrance, and a fragrance which would remain for a long period of time, a chrysanthemum variety having many blooms, and a new and different color of the blooms.

The result of this cross is an entirely new variety of chrysanthemum plant having distinct and unique characteristics distinguishing it from its parents and any other variety known to me.

One of the outstanding characteristics of my new variety is the pronounced jasmine sweet fragrance of the flowers; this fragrance remains for three to four weeks after the flowers have been cut. Another main characteristic of my new variety is the unusual height of the plant, 48 to 56 inches if unpruned, taller than either of its parents by over a foot. A further main characteristic of my new variety is the unusual two-tone color of the blooms. In the open-flower stage, the outside of the petals have a background color of Baryta Yellow overlaid with streaks of Pompeian Red, and the inside of the petals have a background color of Pinard Yellow toward the center of the flower which darkens to an Apricot Yellow as the tips of the flower are approached, this background color is overlaid with streaks of Dragon's Blood Red.

A still further main characteristic of my new variety is the cluster habit which has an unusually large number of blooms, 17 to 20. My new variety blooms earlier than the bronze daisy parent, but later than the "Anemone" parent. The blooming period of my new variety is almost double the length of either of its parents, and yields three crops, while neither parent will yield more than one crop.

Finally, my new variety is resistant to mildew. I have exposed my new variety to mildewed chrysanthemum plants of other varieties in close proximity during the entire blooming period of my new variety, from the end of November until the first of April, under moist conditions and temperatures varying from 38 degrees Fahrenheit to 80 degrees Fahrenheit. No mildew was observed on my new variety, which was grown in Los Angeles, California.

I have performed asexual reproduction of this new variety of chrysanthemum plant at Los Angeles, California, by layering and rooting of cuttings through several succeeding generations. All of the foregoing characteristics and distinctions were transmitted true to form through each of the succeeding generations.

The accompanying color photograph shows typical specimens of the vegetation, flowers, and buds of my new variety.

A detailed description of my new variety follows, the references to color being in accordance with Ridgway's Color Standards and Nomenclature.

Parentage: "Anemone" crossed with an unnamed bronze daisy.

Classification: Semi-double intermediate form.

Growth: Upright, strong, tall, ranging in height from 48 to 56 inches if unpruned.

Cold resistance: No testing was made of cold resistance. The plant was cultivated in a frost free climate.

Mildew resistance: No mildew was observed although the new variety was exposed to mildewed chrysanthemum plants of other varieties from the end of November to the first of April, under moist conditions and temperatures varying from 38 to 80 degrees Fahrenheit.

Blooming period: Under the climatic conditions prevailing in Los Angeles, California, the blooming period extends from the end of November until the first of April.

*Flower*

Bud: The bud starts flattened and grows as the petals elongate. The center shows early. Color—Plate 14, Vinaceous-Rufous.

Bloom:

*Size.*—2 to 3 inches.

*Stem.*—Long and stiff, but will cascade at maturity because of its unusual length.

*Form.*—Semi-double intermediate.

*Petalage.*—5–8 rows of petals.

*Fragrance.*—Pronounced jasmine sweet fragrance which lasts until the cut flowers dry up, 3 to 4 weeks.

*Petals.*—Texture—stiff. Form—oval.

*Color.*—Center of flower—Light Orange Yellow, Plate 3. Outer petals—Apricot Yellow, Plate 4. Base of petals—Pinard Yellow, Plate 4. Outside of petals—background of Baryta Yellow, Plate 4, overlaid with streaks of Pompeian Red, Plate 13. Inside of petals—background of Pinard Yellow, Plate 4 toward the center, which darkens toward the tips to Apricot Yellow, Plate 4, overlaid with streaks of Dragon's Blood Red, Plate 13.

*Plant*

Form: Upright, rounded.

Growth: Vigorous and tall; bushy when properly pruned.

Foliage: Mildew resistant and lush.

*Size.*—3 to 5 inches leaf length.

*Quantity.*—Generous.

*Texture.*—Medium grain.

*Color.*—Upper side—Empire Green, Plate 32. Reverse side—Pois Green, Plate 41.

I claim:

A new and distinct variety of chrysanthemum plant, substantially as shown and described herein, characterized particularly as to novelty by the pronounced jasmine sweet fragrance of its flowers, the long duration of the fragrance, the great height of the plant, the cluster habit and the large number of blooms, the distinctive two-tone Baryta Yellow background overlaid with streaks of Pompeian Red general color tonality of the outside of the petals of the open flower and the distinctive two-tone Pinard Yellow background of the center of the inside of the petals darkening to Apricot Yellow towards the tips of the inside of the petals overlaid with streaks of Dragon's Blood Red general color tonality of the inside of the petals of the open flower, and the resistance to mildew of the plant.

No references cited.